United States Patent
Kima et al.

(10) Patent No.: US 10,918,997 B2
(45) Date of Patent: Feb. 16, 2021

(54) FIELD FILTRATION ASSEMBLY FOR INJECTION WATER QUALITY ASSESSMENT AND MONITORING

(71) Applicant: Saudi Arabian Oil Company, Dhahran (SA)

(72) Inventors: Enow Achuo Kima, Ras Tanura (SA); Qassem Al-Momatin, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/358,209

(22) Filed: Mar. 19, 2019

(65) Prior Publication Data

US 2020/0298183 A1 Sep. 24, 2020

(51) Int. Cl.
| | | |
|---|---|---|
| *B01D 65/10* | (2006.01) | |
| *B01D 61/18* | (2006.01) | |
| *B01D 61/22* | (2006.01) | |
| *C02F 1/44* | (2006.01) | |
| *G01N 15/08* | (2006.01) | |

(52) U.S. Cl.
CPC ............. *B01D 65/10* (2013.01); *B01D 61/18* (2013.01); *B01D 61/22* (2013.01); *C02F 1/444* (2013.01); *G01N 15/0826* (2013.01); *B01D 2313/18* (2013.01); *C02F 2209/03* (2013.01); *C02F 2209/40* (2013.01); *G01N 2015/084* (2013.01)

(58) Field of Classification Search
None
See application file for complete search history.

(56) References Cited

U.S. PATENT DOCUMENTS

| 5,259,960 | A | * | 11/1993 | Beck | ..................... | B01D 61/16 |
|---|---|---|---|---|---|---|
| | | | | | | 210/638 |
| 6,018,989 | A | * | 2/2000 | Kubbillum | ............ | D21F 1/0009 |
| | | | | | | 73/53.04 |
| 2010/0133204 | A1 | | 6/2010 | Tehrani et al. | | |

(Continued)

OTHER PUBLICATIONS

Energy American Petroleum Institute (API), "Recommended Practice for Analysis of Oilfield Waters," API Recommended Practice 45, Third Edition, Aug. 1998, 72 pages.

(Continued)

*Primary Examiner* — Richard C Gurtowski
(74) *Attorney, Agent, or Firm* — Fish & Richardson P.C.

(57) ABSTRACT

An adjustable filtration assembly performs water filtration tests from a sample point. A container contains a water solution. An inlet valve enables a flow of the water solution into the container. An adjustable pressure regulator valve regulates the flow. A relief valve releases a portion of the water solution when a pressure of the water solution exceeds a threshold pressure. A differential pressure gauge displays a current pressure reading of the water solution in the container, receives adjustments specifying a specific pressure to be maintained, maintains the specific pressure of the water solution, and triggers the relief valve when the pressure exceeds the specific pressure. An outlet valve, when opened, outputs a measured volume of the water solution. A filter membrane mounted in the outlet valve filters solids from the measured volume. A relative plugging index (RPI) of the water solution is determined based on a weight of the solids.

20 Claims, 6 Drawing Sheets

(56) References Cited

U.S. PATENT DOCUMENTS

2015/0218010 A1   8/2015   Benavides et al.

OTHER PUBLICATIONS

NACE International, "Standard Test Method: Methods for Determining Quality of Subsurface Injection Water Using Membrane Filtration," NACE Standard TM 0175-2015 Item No. 21205, approved Jun. 1976, revised Oct. 22, 2014, 24 pages.
Patton, "Applied Water Technology," chapter 2, pp. 36-43, Campbell Petroleum Series, 1987, 8 pages.
Baskaran et al., "Physiochemical Characterization and analysis of injection water quality during waterflooding at offshore petroleum facilities," Int. J. Chem. Sci., Jan. 2016, 14(4): 2871-2872.
PCT International Search Report and Written Opinion in International Appln. No. PCT/US2020/022622, dated Jun. 30, 2020, 20 pages.

* cited by examiner

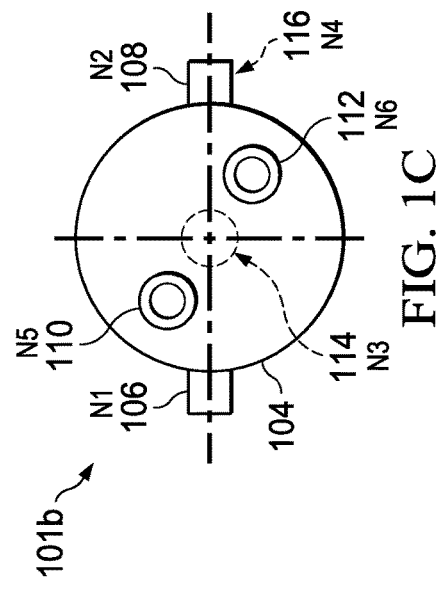
FIG. 1C
| NOZZLE SCHEDULE | | | | |
|---|---|---|---|---|
| MARK | QTY | SIZE | RATING | SERVICE |
| N1 | | 0.5" | 3000 | INLET |
| N2 | | 0.5" | 3000 | OUTLET |
| N3 | | 0.5" | 3000 | DRAIN |
| N4 | | 0.5" | 3000 | SERVICE TEST |
| N5 | | 0.5" | 3000 | PRESSURE GAUGE |
| N6 | | 0.5" | 3000 | RELIEF |
FIG. 1D
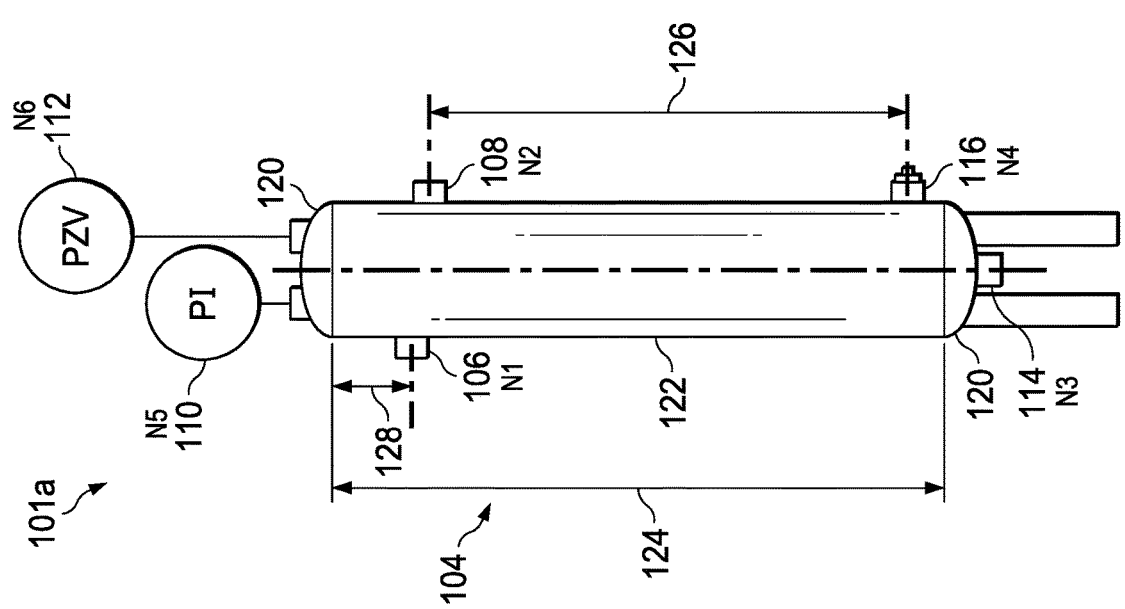
FIG. 1B

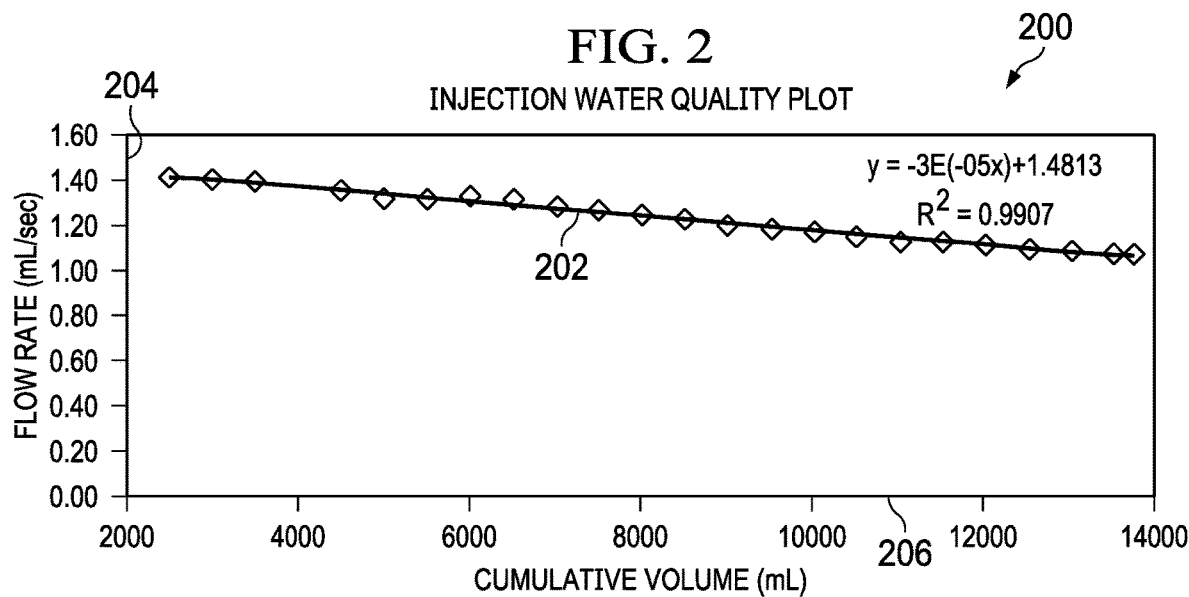
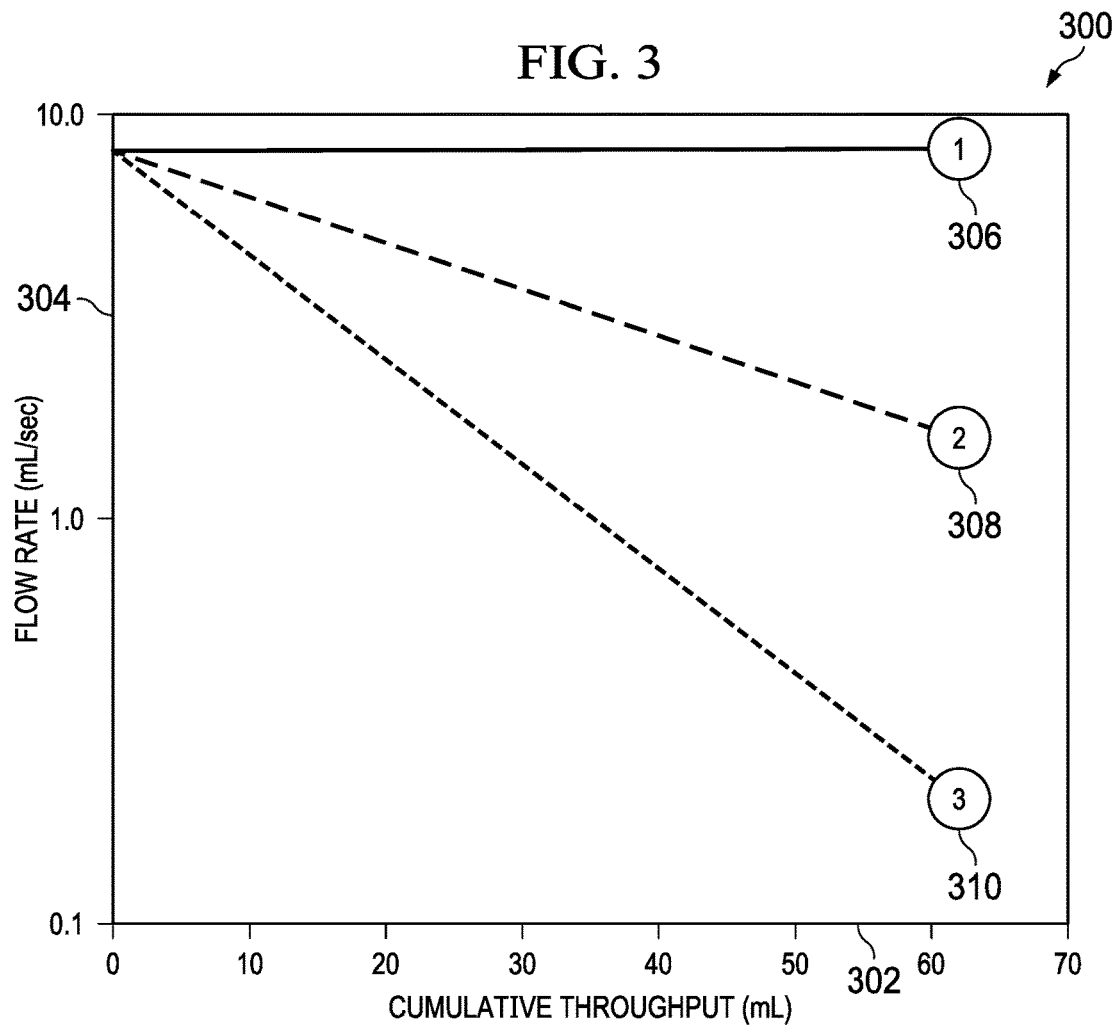

FIELD FILTRATION ASSEMBLY FOR INJECTION WATER QUALITY ASSESSMENT AND MONITORING

BACKGROUND

The present disclosure applies to testing water quality for injection wells. Failure to conduct accurate field filtration test can result in poor assessment and monitoring of the system, poor water quality, high total suspended solids, and a resulting accumulation of deposits that can increase corrosion.

Current industry practices can typically include testing a small volume of sample collected in the field. The volume of the sample can be, for example, 500 milliliters (ml) of water that is collected in a container and sent to a laboratory for testing. The laboratory tests can determine, for example, total suspended solids (TSS), a silt density index (SDI), and other values. During this process, an unmeasurable but significant amount of suspended solids, oil, and grease can be lost to the sample container, such as by clinging to surfaces of the sample container. As a result, laboratory results can be inaccurate and typically do not represent actual conditions in the field.

SUMMARY

The present disclosure describes techniques that can be used for performing field tests of water used in injection wells. In some implementations, an adjustable filtration assembly for performing a water filtration test from a sample point includes the following. A container is configured to contain a water solution being tested by the adjustable filtration assembly. An inlet valve is configured to enable a flow of the water solution from the sample point into the container. An adjustable pressure regulator valve is configured to regulate the flow of the water solution from the inlet valve into the container. A relief valve is configured to release a portion of the water solution from the container when a pressure of the water solution in the container is determined to exceed a threshold pressure. A differential pressure gauge is configured to: display a current pressure reading of the water solution in the container; receive, from an end user, adjustments specifying a specific pressure to be maintained for the water solution in the container; maintain the specific pressure of the water solution passing through the adjustable filtration assembly during the water filtration test; and trigger the relief valve when the pressure of the water solution in the container exceeds the specific pressure. An outlet valve is configured, when opened by the end user, to: output, during a given time period, a measured volume of the water solution from the adjustable filtration assembly; and filter, using a filter membrane mounted in the outlet valve, solids from the measured volume of the water solution, where a relative plugging index (RPI) of the water solution is determined based on a weight of the solids and the given time period.

In some implementations, a computer-implemented method includes the following. An adjustable filtration assembly performs water filtration tests from a sample point. A container contains a water solution. An inlet valve enables a flow of the water solution into the container. An adjustable pressure regulator valve regulates the flow. A relief valve releases a portion of the water solution when a pressure of the water solution exceeds a threshold pressure. A differential pressure gauge displays a current pressure reading of the water solution in the container, receives adjustments specifying a specific pressure to be maintained, maintains the specific pressure of the water solution, and triggers the relief valve when the pressure exceeds the specific pressure. An outlet valve, when opened, outputs a measured volume of the water solution. A filter membrane mounted in the outlet valve filters solids from the measured volume. A relative plugging index (RPI) of the water solution is determined based on a weight of the solids.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method/ the instructions stored on the non-transitory, computer-readable medium.

The subject matter described in this specification can be implemented in particular implementations, so as to realize one or more of the following advantages. First, accurate field filtration tests can result in improved assessment and monitoring of the system. For example, field filtration tests can identify and quantify poor water quality and high total suspended solids, both of which contribute to an accumulation of deposits and potential increases in corrosion. Second, relative plugging index (RPI) values can be determined entirely in the field. Third, the reliability of injection water systems can be improved by improving water quality, enhancing mitigation of corrosion and scaling, and reducing costs and downtime associated with workover of the injection wells. Fourth, a portable apparatus that provides an adjustable filtration assembly can provide accurate, efficient, and reliable water filtration tests.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

FIGS. 1B-1D are schematic diagrams showing example specifications of portable apparatus of FIG. 1A, according to some implementations of the present disclosure.

FIG. 2 is a graph showing an example of a plot of a flow rate versus a cumulative volume, according to some implementations of the present disclosure.

FIG. 3 is a graph showing examples of water quality monitoring curves, according to some implementations of the present disclosure.

Like reference numbers and designations in the various drawings indicate like elements.

DETAILED DESCRIPTION

The following detailed description describes techniques for performing field tests of water used in injection wells. Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

Figure 1A:
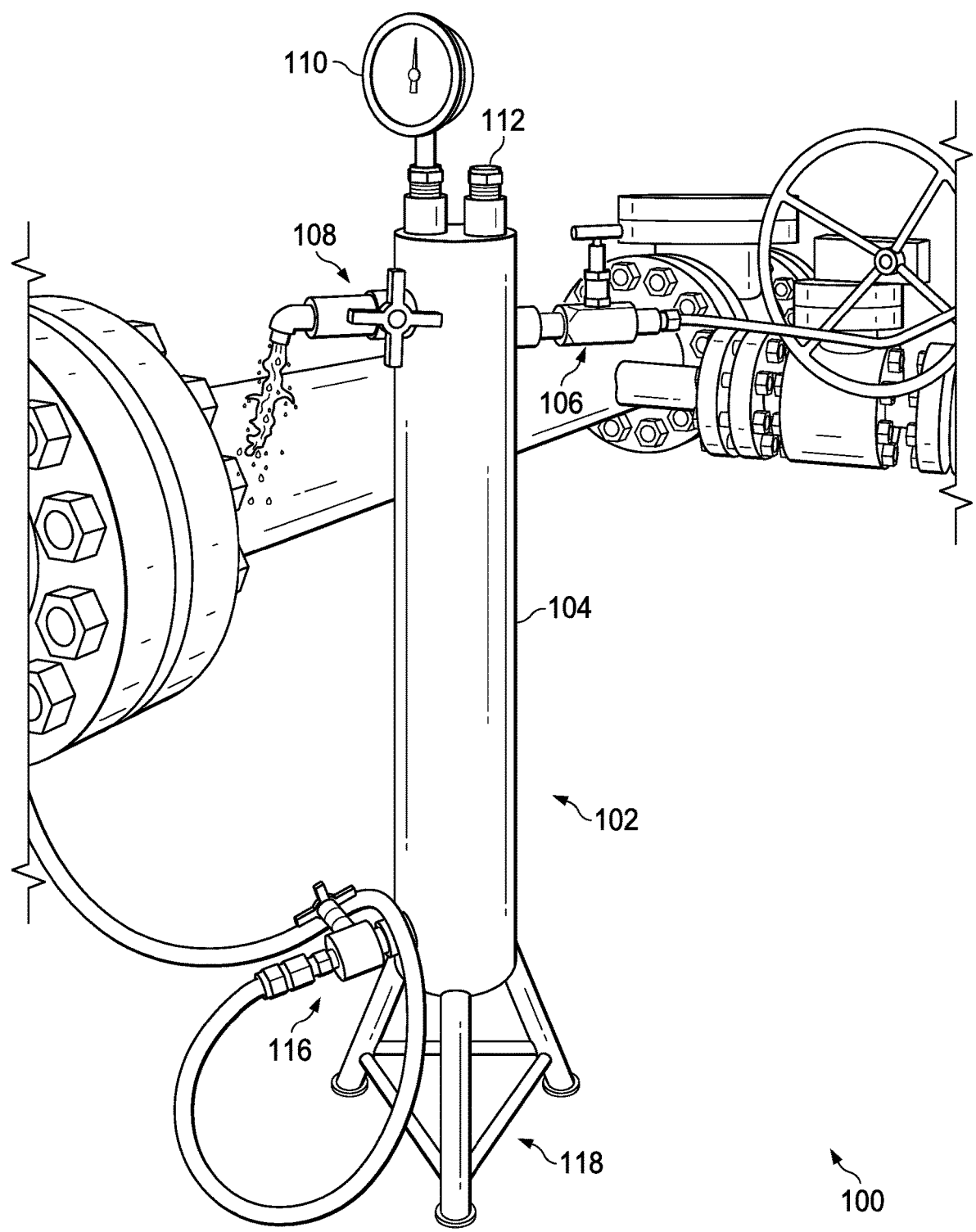
FIG. 1A is a photo showing an example of a portable apparatus for performing field tests of water, according to some implementations of the present disclosure.

FIG. 1A is a photo showing an example of a portable apparatus 102 for performing field tests of water, according to some implementations of the present disclosure. For example, the portable apparatus 102 can be an adjustable filtration assembly that is part of a system 100 for performing field water quality assessment and monitoring at a power water injector (PWI) facility. The portable apparatus 102 includes an adjustable filtration assembly 104. Field tests performed using the portable apparatus 102 can help assess the impact of the suspended solids on flow rates. The field tests can determine the quantities of the total solids present and the tendency of the solids, for example, to plug injection wells.

FIGS. 1B-1D are schematic diagrams showing example specifications of the portable apparatus 102 of FIG. 1A, according to some implementations of the present disclosure. FIG. 1B includes a side view 101a of the adjustable filtration assembly 104. FIG. 1C includes a top view 101b of the adjustable filtration assembly 104. FIG. 1D includes specifications of the adjustable filtration assembly 104. The adjustable filtration assembly 104 can be configured to include an adjustable pressure regulator valve to maintain a specific pressure (for example, 20 pounds per square inch (psi)) during a pre-determined test duration (for example, 30 minutes). For example, the adjustable pressure regulator valve can enable a flow of water solution from the inlet valve into the container. During a field test being performed using the portable apparatus 102, a container in the adjustable filtration assembly 104 can contain a water solution that is being tested. An inlet valve 106 and an outlet valve 108 of the adjustable filtration assembly 104 can control entry and exist of the water solution through the adjustable filtration assembly 104. The adjustable filtration assembly 104 can include a differential pressure gauge 110 (for example, 30 psi max), a low-pressure relief valve 112 (for example, set at 30 per square inch gauge (psig)), and an outlet valve 108. The outlet valve 108 can be used during a field test to allow excess water that flows through the outlet valve 108. A drain 114 can be used to drain the adjustable filtration assembly 104, for example, after a field test. A service test outlet 116 can include a flow meter and totalizer configured to measure the flow rate and the cumulative volume, for example, volume of water can indicate the amount of water that passes through a filter membrane (for example, 0.45 micron) within a membrane holder that is part of the service test outlet 116, for example, to perform service on the adjustable filtration assembly 104. The adjustable filtration assembly 104 can be mounted on a stand 118.

In some implementations, the adjustable filtration assembly 104 and its components can have the following dimensions. Caps 120 (measuring, for example, three inches in diameter) can be used to cap ends of a cylindrical chamber 122 (measuring, for example, three inches in diameter, with a length 124 of 16 inches). The caps 120 can be welded to the cylindrical chamber 122, for example. Centers of the outlet valve 108 and the service test outlet 116 that are relative to their placement on the adjustable filtration assembly 104 can be separated by a distance 126 (measuring, for example, 12.5 inches). A center of the inlet valve 106 relative to the valve's placement on the adjustable filtration assembly 104 can be separated from the top of the cylindrical chamber 122 by a distance 128 of two inches, for example. Nozzles 130 (including threaded welding bosses) used for the inlet 106, the outlet 108, the drain 114, the service test outlet 116, the differential pressure gauge 110, and the relief valve 112 can have a 0.5 inch diameter 132, as shown in a nozzle schedule 134. Other dimensions of adjustable filtration assembly 104 and its components are possible, for example, in order to handle a different amount water that is tested.

In some implementations, the portable apparatus 102 can be used to conduct water quality assessment and monitoring by filtering a known volume of water through the portable apparatus 102, for example at a constant pressure of 20 psig for 30 minutes. The portable apparatus 102 can be connected to a sample point of interest. Sample points can include, for example, supply well flowlines, upstream filters, downstream filters, and upstream injection water wells. During a field test, a known volume of water from the sample point can be allowed to flow into the portable apparatus 102. The water can enter the inlet valve 106 and flow through the outlet valve 108, flowing through the filtration membrane. For example, the filtration membrane can include a 0.45 micron filter element. The field test can be conducted at 20 psig and can cover a 30-minute test duration, for example. The volume of the filtered water through the membrane can be measured, for example, using a 4.0 L measuring cylinder. A time required to fill the measuring cylinder with a predetermined volume (for example, 500 ml) can be recorded.

The portable apparatus 102 can be used to monitor water quality and to determine a relative plugging index (RPI) of the water being tested. On-site testing made possible by the portable apparatus 102 can allow operations at the site to more quickly make changes that can correct conditions that lead to corrosion due to high content of total suspended solids and deposits. For example, use of the portable apparatus 102 and the information that is provided through the use can improve water conditioning and reduce corrosion due to suspended solids and deposits. Field results using the portable apparatus 102 are provided in FIGS. 2-3.

Users of the portable apparatus 102 can receive proper training in the use of the portable apparatus 102 and the adjustable filtration assembly 104. For example, the training can inform users of proper procedures for introducing water to the adjustable filtration assembly 104. The training can also inform user how to install, remove, and weigh the filter used during the field tests.

FIG. 2 is a graph 200 showing an example of a plot 202 of a flow rate 204 versus a cumulative volume 206, according to some implementations of the present disclosure. The plot 202 is an approximation line connecting individual data points obtained from field filtration tests conducted at an example XYZ facility. The facility's power water injector (PWI) system can have an RPI of 21.3, for example. An RPI value resulting from the tests is a high RPI indicating an impairment of injectivity of the water injection well. Generally, RPI values can be interpreted using ratings associated with ranges of RPI values, including RPI<3 (excellent rating), RPI in 3-10 range (good rating), RPI in 10-15 range (bad rating), and RPI>15 (poor rating). Other data associated with the test results includes a total suspended solids (TSS) of 4.2 milligrams per liter (mg/l), a millipore test slope number (MTSN)=−25.5, and an RPI of 21.3.

The XYZ site was selected for the field filtration tests because of numerous failures due to corrosion, suspended solids, and deposits accumulation. Conducting the field filtration tests included measuring a filtered volume over a specific length of time. The volume and time information were used with a weight of the membrane element to calculate a total suspended solids content and the RPI.

Information that is learned from the tests can be used, for example, to facilitate the assessment and monitoring of the injection water quality. The information can also mandate the conditioning of the system in order to reduce the amount of suspended solids, decrease the corrosion rate, and meet water quality specifications. The portable apparatus 102 can make it possible to assess and monitor the water quality of injection water system at other facilities. The portable apparatus 102 can be used instead of conventional practices of using silt density index (SDI), which has a lag time associated with waiting for lab results. Using the portable apparatus 102 can result in conditioning and improving the water quality injection water system, and improving the reliability of the injection water system.

FIG. 1 is a graph showing examples of water quality monitoring curves 300, according to some implementations of the present disclosure. The quality monitoring curves 300 are plotted relative to a cumulative throughput 302 (for example, through the outlet valve 108) and a flow rate 304 (for example, through the inlet valve 106). Throughputs and flow rates can be measured in milliliters (mL), for example. The flow rate 304 is relative to a log scale. The log scale highlights differences between quality monitoring curves 306, 308, and 310. For example, the quality monitoring curve 306 can correspond to conditions in which the RPI value is extremely low. The quality monitoring curves 308 and 310 can correspond to conditions in which the RPI values are significantly greater, the quality monitoring curve 310 corresponding to the greatest RPI value among the quality monitoring curves 302, 304, and 306.

Figure 4A:
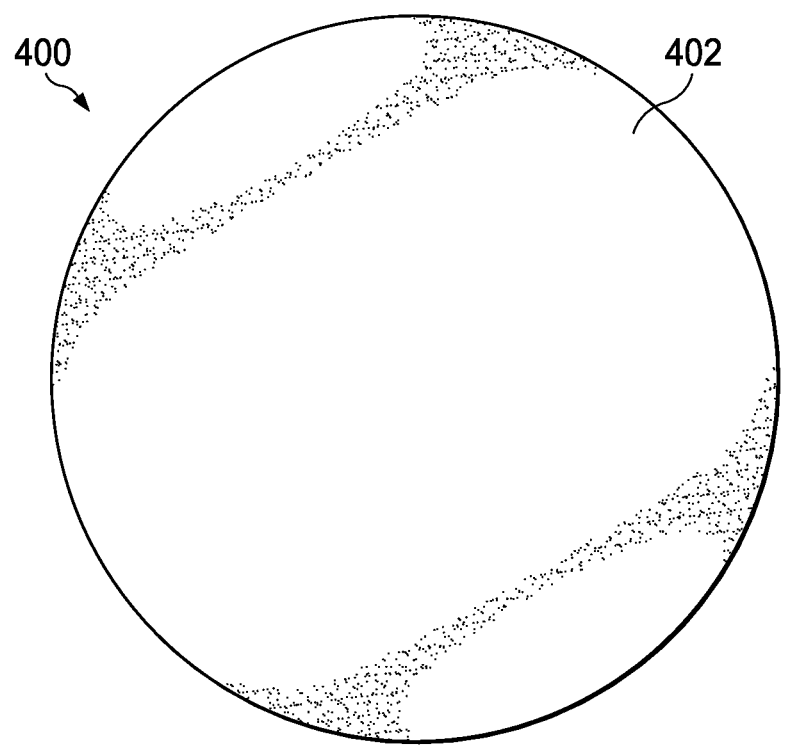
FIG. 4A is an image showing an example of a filter before a filtration test, according to some implementations of the present disclosure.

FIG. 4A is an image 400 showing an example of a filter 402 before a filtration test, according to some implementations of the present disclosure. For example, the filter 402 can be a millipore filter paper. Prior to a filtration test, the filter 402 can be placed in a membrane holder that is part of the outlet valve 108.

Figure 4B:
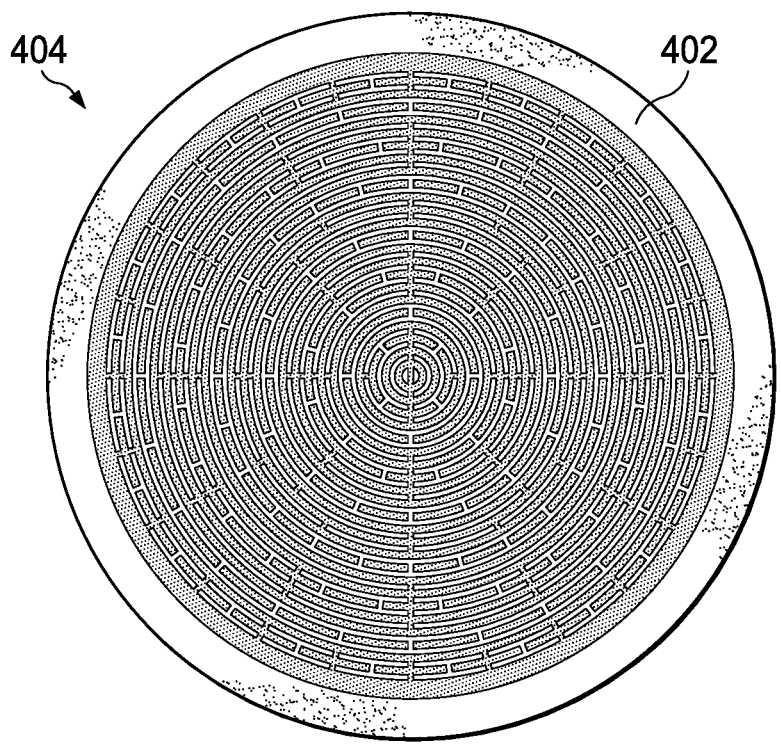
FIG. 4B is an image showing an example of the filter after the filtration test, according to some implementations of the present disclosure.

FIG. 4B is an image 404 showing an example of the filter 402 after the filtration test, according to some implementations of the present disclosure. The filter 402 shown in the image 404 includes solids that have been trapped by the filter 402 during a filtration test. The weight of the solids (for example, determined based on a known starting weight of the filter 402) can be used to determine, for example, a RPI for the water being tested. The starting weight of the filter 402 can be a wet weight, for example, to more accurately determine the weight of solids that are present.

Figure 5:
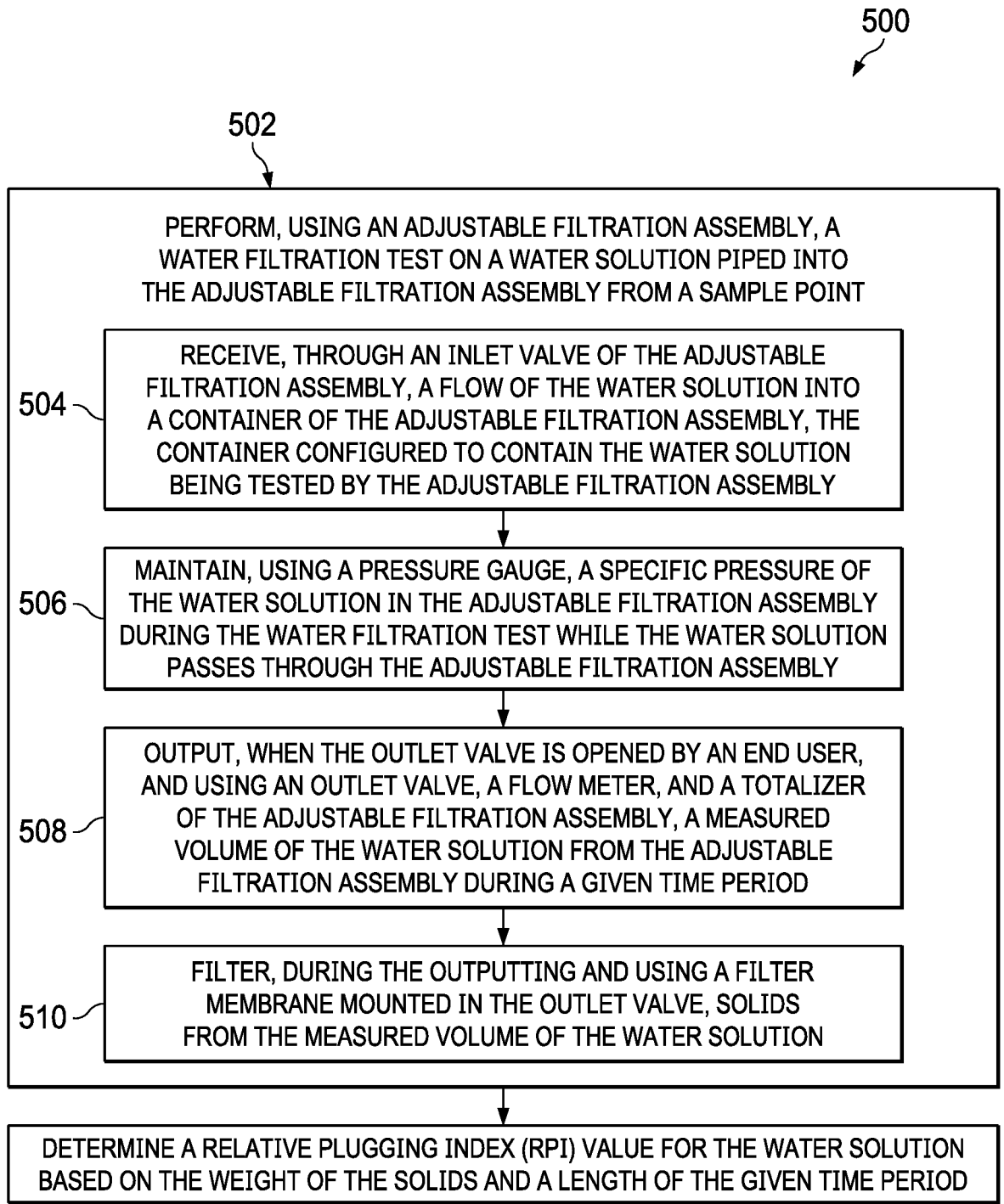
FIG. 5 is a flow diagram of an example of a method for performing a water filtration test, according to some implementations of the present disclosure.

FIG. 5 is a flowchart of an example method 500 for performing a water filtration test, according to some implementations of the present disclosure. For clarity of presentation, the description that follows generally describes method 500 in the context of the other figures in this description. However, it will be understood that method 500 may be performed, for example, by any suitable system, environment, software, and hardware, or a combination of systems, environments, software, and hardware, as appropriate. In some implementations, various steps of method 500 can be run in parallel, in combination, in loops, or in any order.

At 502, using an adjustable filtration assembly, a water filtration test is performed on a water solution piped into the adjustable filtration assembly from a sample point. For example, the water filtration test can be performed at a power water injector (PWI) facility using the portable apparatus 102. The water filtration test can include steps 504-510. From 502, method 500 proceeds to 504.

At 504, a flow of the water solution is received through an inlet valve of the adjustable filtration assembly into a container of the adjustable filtration assembly. The container is configured to contain the water solution being tested by the adjustable filtration assembly. For example, the inlet valve 106 of the adjustable filtration assembly 104 can be opened allowing a water solution to flow into the container in the adjustable filtration assembly 104. In some implementations, the water solution can be provided to the adjustable filtration assembly 104 through a hose connected to a sample point such as a supply well flowline, and upstream filter, a downstream filter, or an upstream injection water well. The portable apparatus 102 can be located in close proximity to the sample point. From 504, method 500 proceeds to 506.

At 506, a specific pressure of the water solution in the adjustable filtration assembly is maintained using a pressure gauge during the water filtration test while the water solution passes through the adjustable filtration assembly. As an example, the differential pressure gauge 110 can be used to maintain the water solution inside of the adjustable filtration assembly 104 at or near a constant pressure (for example, 30 psi max). From 506, method 500 proceeds to 508.

At 508, a measured volume of the water solution from the adjustable filtration assembly is output during a given time period using an outlet valve of the adjustable filtration assembly when the outlet valve is opened by an end user. For example, when a user opens the outlet valve 108, the water filtration test can be initiated to filter a measurable amount of water over a given time period (for example, 30 minutes). From 508, method 500 proceeds to 510.

At 510, using a filter membrane mounted in the outlet valve, solids are filtered from the measured volume of the water solution. For example, during the water filtration test, a 0.45 micron filter membrane mounted within a membrane holder can filter solids from the water solution that is filtered through the filter membrane. From 510, method 500 proceeds to 512.

At 512, a relative plugging index (RPI) value is determined for the water solution based on the weight of the solids and a length of the given time period. For example, the RPI can be calculated based on a volume of the water solution that has passed through the filter. In some implementations, other measures associated with water quality can be calculated. After 512, method 500 can stop.

Figure 6:
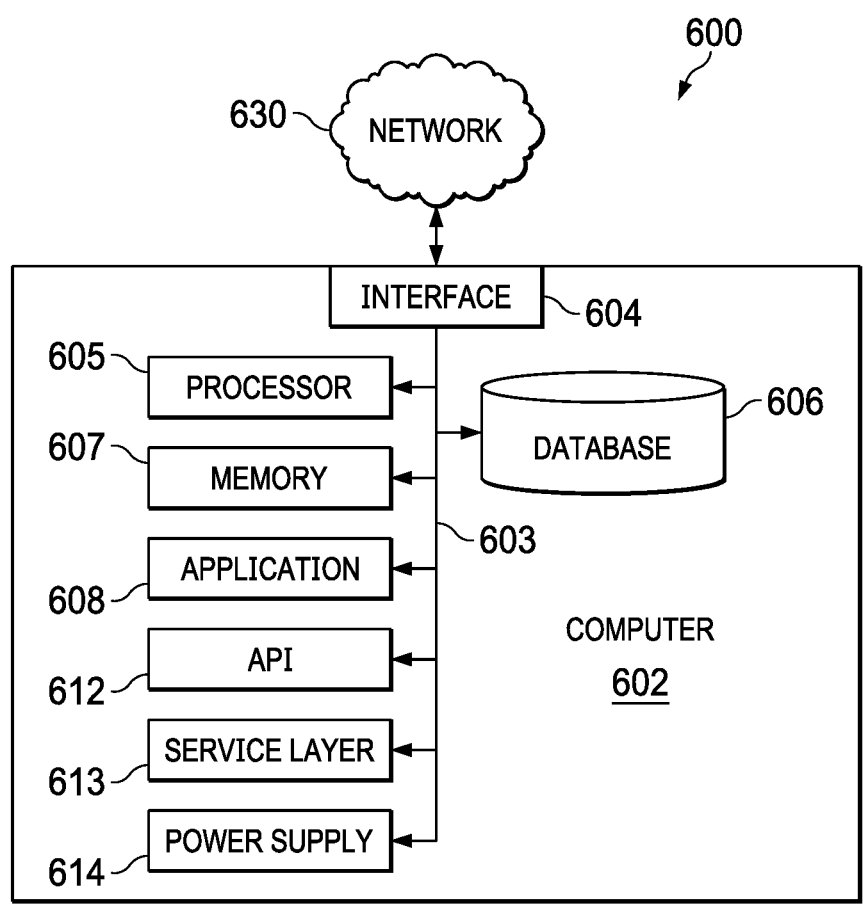
FIG. 6 is a block diagram illustrating an example computer system used to provide computational functionalities associated with described algorithms, methods, functions, processes, flows, and procedures as described in the instant disclosure, according to some implementations of the present disclosure.

FIG. 6 is a block diagram of an example computer system 600 used to provide computational functionalities associated with described algorithms, methods, functions, processes, flows, and procedures, as described in the instant disclosure, according to some implementations of the present disclosure. The illustrated computer 602 is intended to encompass any computing device such as a server, desktop computer, laptop/notebook computer, wireless data port, smart phone, personal data assistant (PDA), tablet computing device, one or more processors within these devices, or any other suitable processing device, including physical or virtual instances (or both) of the computing device. Additionally, the computer 602 can include a computer that includes an input device, such as a keypad, keyboard, or a touch screen that can accept user information, and an output device that conveys information associated with the operation of the computer 602, including digital data, visual, or audio information (or a combination of information), or a graphical-type user interface (UI) (or GUI).

The computer 602 can serve in a role as a client, network component, a server, a database, a persistency, or components of a computer system for performing the subject matter described in the instant disclosure. The illustrated computer 602 is communicably coupled with a network 630. In some implementations, one or more components of the computer 602 may be configured to operate within environments, including cloud-computing-based, local, global, and a combination of environments.

At a high level, the computer 602 is an electronic computing device operable to receive, transmit, process, store, or manage data and information associated with the described subject matter. According to some implementations, the computer 602 may also include or be communicably coupled with an application server, email server, web server, caching server, streaming data server, or a combination of servers.

The computer 602 can receive requests over network 630 from a client application (for example, executing on another computer 602) and respond to the received requests by processing the received requests using an appropriate software application(s). In addition, requests may also be sent to the computer 602 from internal users (for example, from a command console), external or third-parties, automated applications, entities, individuals, systems, or computers.

Each of the components of the computer 602 can communicate using a system bus 603. In some implementations, any or all of the components of the computer 602, hardware or software (or a combination of both hardware and software), may interface with each other or the interface 604 (or a combination of both), over the system bus 603 using an application programming interface (API) 612 or a service layer 613 (or a combination of the API 612 and service layer 613). The API 612 may include specifications for routines, data structures, and object classes. The API 612 may be either computer-language independent or dependent and refer to a complete interface, a single function, or even a set of APIs. The service layer 613 provides software services to the computer 602 and other components (whether or not illustrated) that are communicably coupled to the computer 602. The functionality of the computer 602 may be accessible for all service consumers using this service layer. Software services, such as those provided by the service layer 613, provide reusable, defined functionalities through a defined interface. For example, the interface may be software written in JAVA, C++, or a language providing data in extensible markup language (XML) format. While illustrated as an integrated component of the computer 602, alternative implementations may illustrate the API 612 or the service layer 613 as stand-alone components in relation to other components of the computer 602 and other components communicably coupled to the computer 602. Moreover, any or all parts of the API 612 or the service layer 613 may be implemented as child or sub-modules of another software module, enterprise application, or hardware module without departing from the scope of this disclosure.

The computer 602 includes an interface 604. Although illustrated as a single interface 604 in FIG. 6, two or more interfaces 604 may be used according to particular needs, desires, or particular implementations of the computer 602. The interface 604 is used by the computer 602 for communicating with other systems that are connected to the network 630 (whether illustrated or not) in a distributed environment. Generally, the interface 604 includes logic encoded in software or hardware (or a combination of software and hardware) and is operable to communicate with the network 630. More specifically, the interface 604 can include software supporting one or more communication protocols associated with communications such that the network 630 or interface's hardware is operable to communicate physical signals within and outside of the illustrated computer 602.

The computer 602 includes a processor 605. Although illustrated as a single processor 605 in FIG. 6, two or more processors may be used according to particular needs, desires, or particular implementations of the computer 602. Generally, the processor 605 executes instructions and manipulates data to perform the operations of the computer 602 and any algorithms, methods, functions, processes, flows, and procedures as described in the instant disclosure.

The computer 602 also includes a database 606 that can hold data for the computer 602 and other components connected to the network 630 (whether illustrated or not). For example, database 606 can be an in-memory, conventional, or a database storing data consistent with this disclosure. In some implementations, database 606 can be a combination of two or more different database types (for example, a hybrid in-memory and conventional database) according to particular needs, desires, or particular implementations of the computer 602 and the described functionality. Although illustrated as a single database 606 in FIG. 6, two or more databases (of the same or combination of types) can be used according to particular needs, desires, or particular implementations of the computer 602 and the described functionality. While database 606 is illustrated as an integral component of the computer 602, in alternative implementations, database 606 can be external to the computer 602.

The computer 602 also includes a memory 607 that can hold data for the computer 602 or a combination of components connected to the network 630 (whether illustrated or not). Memory 607 can store any data consistent with this disclosure. In some implementations, memory 607 can be a combination of two or more different types of memory (for example, a combination of semiconductor and magnetic storage) according to particular needs, desires, or particular implementations of the computer 602 and the described functionality. Although illustrated as a single memory 607 in FIG. 6, two or more memories 607 (of the same or combination of types) can be used according to particular needs, desires, or particular implementations of the computer 602 and the described functionality. While memory 607 is illustrated as an integral component of the computer 602, in alternative implementations, memory 607 can be external to the computer 602.

The application 608 is an algorithmic software engine providing functionality according to particular needs, desires, or particular implementations of the computer 602, particularly with respect to functionality described in this disclosure. For example, application 608 can serve as one or more components, modules, or applications. Further, although illustrated as a single application 608, the application 608 may be implemented as multiple applications 608 on the computer 602. In addition, although illustrated as integral to the computer 602, in alternative implementations, the application 608 can be external to the computer 602.

The computer 602 can also include a power supply 614. The power supply 614 can include a rechargeable or non-rechargeable battery that can be configured to be either user- or non-user-replaceable. In some implementations, the power supply 614 can include power-conversion or management circuits (including recharging, standby, or a power management functionality). In some implementations, the power-supply 614 can include a power plug to allow the computer 602 to be plugged into a wall socket or a power source to, for example, power the computer 602 or recharge a rechargeable battery.

There may be any number of computers 602 associated with, or external to, a computer system containing computer 602, each computer 602 communicating over network 630. Further, the term "client," "user," and other appropriate terminology may be used interchangeably, as appropriate, without departing from the scope of this disclosure. Moreover, this disclosure contemplates that many users may use one computer 602, or that one user may use multiple computers 602.

Described implementations of the subject matter can include one or more features, alone or in combination.

For example, in a first implementation, an adjustable filtration assembly is configured to perform a water filtration test from a sample point. A container is configured to contain a water solution being tested by the adjustable filtration assembly. An inlet valve is configured to enable a flow of the water solution from the sample point into the container. An adjustable pressure regulator valve is configured to regulate the flow of the water solution from the inlet valve into the container. A relief valve is configured to release a portion of the water solution from the container when a pressure of the water solution in the container is determined to exceed a threshold pressure. A differential pressure gauge is configured to: display a current pressure reading of the water solution in the container; receive, from an end user, adjustments specifying a specific pressure to be maintained for the water solution in the container; maintain the specific pressure of the water solution passing through the adjustable filtration assembly during the water filtration test; and trigger the relief valve when the pressure of the water solution in the container exceeds the specific pressure. An outlet valve is configured, when opened by the end user, to: output, during a given time period, a measured volume of the water solution from the adjustable filtration assembly; and filter, using a filter membrane mounted in the outlet valve, solids from the measured volume of the water solution, where a relative plugging index (RPI) of the water solution is determined based on a weight of the solids and the given time period.

The foregoing and other described implementations can each, optionally, include one or more of the following features:

A first feature, combinable with any of the following features, where the water filtration test is a local field test included in field water quality assessment and monitoring at a power water injector (PWI) facility, and where the water filtration test is completed within minutes without sending the water solution to a lab.

A second feature, combinable with any of the previous or following features, where the adjustable filtration assembly further includes a drain that, when activated, drains the water solution from the adjustable filtration assembly.

A third feature, combinable with any of the previous or following features, where the adjustable filtration assembly further includes a service test outlet configured to facilitate service on the adjustable filtration assembly.

A fourth feature, combinable with any of the previous or following features, further including a stand supporting the adjustable filtration assembly.

A fifth feature, combinable with any of the previous or following features, where sample points include supply well flowlines, upstream filters, downstream filters, and upstream injection water wells.

A sixth feature, combinable with any of the previous or following features, where the water filtration test is performed at 20 per square inch gauge (psig) for 30 minutes.

In a second implementation, a method includes the following. Using an adjustable filtration assembly, a water filtration test is performed on a water solution piped into the adjustable filtration assembly from a sample point. A flow of the water solution is received through an inlet valve of the adjustable filtration assembly into a container of the adjustable filtration assembly. The container is configured to contain the water solution being tested by the adjustable filtration assembly. A specific pressure of the water solution in the adjustable filtration assembly is maintained using a pressure gauge during the water filtration test while the water solution passes through the adjustable filtration assembly. A measured volume of the water solution from the adjustable filtration assembly is output during a given time period using an outlet valve of the adjustable filtration assembly when the outlet valve is opened by an end user. Using a filter membrane mounted in the outlet valve, solids are filtered from the measured volume of the water solution. A relative plugging index (RPI) value is determined for the water solution based on the weight of the solids and a length of the given time period.

The foregoing and other described implementations can each, optionally, include one or more of the following features:

A first feature, combinable with any of the previous or following features, where the method further includes releasing, by a relief valve on the adjustable filtration assembly, a portion of the water solution when a pressure of the water solution in the container exceeds a threshold pressure.

A second feature, combinable with any of the previous or following features, where the method further includes displaying a current pressure reading of the water solution in the container.

A third feature, combinable with any of the previous or following features, where the method further includes receiving, from the end user, adjustments specifying a specific pressure at which to maintain the pressure of the water solution in the container.

A fourth feature, combinable with any of the previous or following features, where the adjustable filtration assembly is attached to and supported by a stand.

A fifth feature, combinable with any of the previous or following features, where sample points include supply well flowlines, upstream filters, downstream filters, and upstream injection water wells.

A sixth feature, combinable with any of the previous or following features, where the water filtration test is performed at 20 per square inch gauge (psig) for 30 minutes.

In a third implementation, a non-transitory, computer-readable medium storing one or more instructions executable by a computer system to perform operations including the following. Using an adjustable filtration assembly, a water filtration test is performed on a water solution piped into the adjustable filtration assembly from a sample point. A flow of the water solution is received through an inlet valve of the adjustable filtration assembly into a container of the adjustable filtration assembly. The container is configured to contain the water solution being tested by the adjustable filtration assembly. A specific pressure of the water solution in the adjustable filtration assembly is maintained using a pressure gauge during the water filtration test while the water solution passes through the adjustable filtration assembly. A measured volume of the water solution from the adjustable filtration assembly is output during a given time period using an outlet valve of the adjustable filtration assembly when the outlet valve is opened by an end user. Using a filter membrane mounted in the outlet valve, solids are filtered from the measured volume of the water solution. A relative plugging index (RPI) value is determined for the water solution based on the weight of the solids and a length of the given time period.

The foregoing and other described implementations can each, optionally, include one or more of the following features:

A first feature, combinable with any of the previous or following features, where the operations further include releasing, by a relief valve on the adjustable filtration assembly, a portion of the water solution when a pressure of the water solution in the container exceeds a threshold pressure.

A second feature, combinable with any of the previous or following features, where the operations further include displaying a current pressure reading of the water solution in the container.

A third feature, combinable with any of the previous or following features, where the operations further include receiving, from the end user, adjustments specifying a specific pressure at which to maintain the pressure of the water solution in the container.

A fourth feature, combinable with any of the previous or following features, where the adjustable filtration assembly is attached to and supported by a stand.

A fifth feature, combinable with any of the previous or following features, where sample points include supply well flowlines, upstream filters, downstream filters, and upstream injection water wells.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs, that is, one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal, for example, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include, special purpose logic circuitry. Circuitry can include, for example, a central processing unit (CPU), a field programmable gate array (FPGA), or an application-specific integrated circuit (ASIC). In some implementations, the data processing apparatus or special purpose logic circuitry (or a combination of the data processing apparatus or special purpose logic circuitry) may be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which may also be referred to or described as a program, software, a software application, a module, a software module, a script, or code can be written in any form of programming language, including compiled or interpreted languages, or declarative or procedural languages, and it can be deployed in any form, including as a stand-alone program or as a module, component, subroutine, or a unit for use in a computing environment. A computer program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or processes, the programs may instead include a number of sub-modules, third-party services, components, libraries, and such, as appropriate. Conversely, the features and functionality of various components can be combined into single components, as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on general or special purpose microprocessors, or both. Generally, a CPU will receive instructions and data from and write to a memory. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data includes all forms of permanent/non-permanent or volatile/non-volatile memory, media and memory devices, including by way of example semiconductor memory devices, for example, random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices; magnetic devices, for example, tape, cartridges, cassettes, internal/removable disks; magneto-optical disks; and optical memory devices, for example, digital video disc (DVD), CD-ROM, DVD+/-R, DVD-RAM, DVD-ROM, HD-DVD, and BLURAY. The memory may store various objects or data, including caches, classes, frameworks, applications, modules, backup data, jobs, web pages, web page templates, data structures, database tables, repositories storing dynamic information, including parameters, variables, algorithms, instructions, rules, constraints, and references. Additionally, the memory may include logs, policies, security or access data, and reporting files. The processor and the memory can be supplemented by, or incorporated in, special purpose logic circuitry.

To provide for interaction with a user, implementations of the subject matter described in this specification can be implemented on a computer having a display device, for example, a cathode ray tube (CRT), liquid crystal display (LCD), light-emitting diode (LED), or plasma monitor, for displaying information to the user and a keyboard and a pointing device, for example, a mouse, trackball, or trackpad by which the user can provide input to the computer. Input may also be provided to the computer using a touchscreen, such as a tablet computer surface with pressure sensitivity, a multi-touch screen using capacitive or electric sensing. Devices can be used to provide for interaction with a user. Feedback provided to the user can be any form of sensory feedback, for example, visual feedback, auditory feedback, or tactile feedback. Input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons. UI elements may be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with some implementations of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20 protocols), all or a portion of the Internet, communication systems at one or more locations, or a combination of communication networks. The network may communicate with, for example, Internet Protocol (IP) packets, Frame Relay frames, Asynchronous Transfer Mode (ATM) cells, voice, video, data, or a combination of communication types between network addresses.

The computing system can include clients and servers. A client and server are generally remote from each other and typically interact through a communication network. The relationship of client and server arises by virtue of computer programs running on the respective computers and having a client-server relationship to each other.

Cluster file systems can be any file system type accessible from multiple servers for read and update. Locking or consistency tracking may not be necessary since the locking of exchange file system can be done at application layer. Furthermore, Unicode data files are different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain this disclosure. Other changes, substitutions, and alterations are also possible without departing from the spirit and scope of this disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. An adjustable filtration assembly for performing a water filtration test from a sample point, comprising:
   a container configured to contain a water solution being tested by the adjustable filtration assembly;
   an inlet valve configured to enable a flow of the water solution from the sample point into the container;
   an adjustable pressure regulator valve is configured to regulate the flow of the water solution from the inlet valve into the container;
   a relief valve configured to release a portion of the water solution from the container when a pressure of the water solution in the container is determined to exceed a threshold pressure;
   a differential pressure gauge configured to:
      display a current pressure reading of the water solution in the container;
      receive, from an end user, adjustments specifying a specific pressure to be maintained for the water solution in the container;
      maintain the specific pressure of the water solution passing through the adjustable filtration assembly during the water filtration test; and
      trigger the relief valve when the pressure of the water solution in the container exceeds the specific pressure; and
   an outlet valve configured, when opened by the end user, to:
      output, during a given time period, a measured volume of the water solution from the adjustable filtration assembly; and
      filter, using a filter membrane mounted in the outlet valve, solids from the measured volume of the water solution, wherein a relative plugging index (RPI) of the water solution is determined based on a weight of the solids and the given time period, and wherein the weight of the solids is determined using the measured volume and a starting wet weight of the filter membrane.

2. The adjustable filtration assembly of claim 1, wherein the water filtration test is a local field test included in field water quality assessment and monitoring at a power water injector (PWI) facility, and wherein the water filtration test is completed without sending the water solution to a lab.

3. The adjustable filtration assembly of claim 1, wherein the adjustable filtration assembly further comprises a drain that, when activated, drains the water solution from the adjustable filtration assembly.

4. The adjustable filtration assembly of claim 1, wherein the adjustable filtration assembly further comprises a service test outlet configured to facilitate service on the adjustable filtration assembly.

5. The adjustable filtration assembly of claim 1, further comprising a stand supporting the adjustable filtration assembly.

6. The adjustable filtration assembly of claim 1, wherein the sample point is selected from sample points of supply well flowlines, upstream filters, downstream filters, and upstream injection water wells.

7. The adjustable filtration assembly of claim 1, wherein the water filtration test is performed at 20 per square inch gauge (psig), maintained by the adjustable pressure regulator valve, for 30 minutes.

8. A method, comprising:
   performing, using an adjustable filtration assembly, a water filtration test on a water solution piped into the adjustable filtration assembly from a sample point, the water filtration test comprising:
      receiving, through an inlet valve of the adjustable filtration assembly, a flow of the water solution into a container of the adjustable filtration assembly, the container configured to contain the water solution being tested by the adjustable filtration assembly;
      maintaining, using a pressure gauge, a specific pressure of the water solution in the adjustable filtration assembly during the water filtration test while the water solution passes through the adjustable filtration assembly;
      outputting, using an outlet valve of the adjustable filtration assembly when the outlet valve is opened by an end user, a flow meter and totalizer to measure a volume of the water solution from the adjustable filtration assembly during a given time period; and
      filtering, during the outputting and using a filter membrane mounted in the outlet valve, solids from a measured volume of the water solution; and
   determining a relative plugging index (RPI) value for the water solution based on a weight of the solids and a length of the given time period, wherein the weight of the solids is determined using the measured volume and a starting wet weight of the filter membrane.

9. The method of claim 8, further comprising releasing, by a relief valve on the adjustable filtration assembly, a portion of the water solution when a pressure of the water solution in the container exceeds a threshold pressure.

10. The method of claim 8, further comprising displaying a current pressure reading of the water solution in the container.

11. The method of claim 8, further comprising receiving, from the end user, adjustments specifying a specific pressure at which to maintain a pressure of the water solution in the container.

12. The method of claim 8, wherein the adjustable filtration assembly is attached to and supported by a stand.

13. The method of claim 8, wherein the sample point is selected from sample points of supply well flowlines, upstream filters, downstream filters, and upstream injection water wells.

14. The method of claim 8, wherein the water filtration test is performed at 20 per square inch gauge (psig), maintained by an adjustable pressure regulator valve, for 30 minutes.

15. A non-transitory, computer-readable medium storing one or more instructions executable by a computer system to perform operations comprising:

performing, using an adjustable filtration assembly, a water filtration test on a water solution piped into the adjustable filtration assembly from a sample point, the water filtration test comprising:

receiving, through an inlet valve of the adjustable filtration assembly, a flow of the water solution into a container of the adjustable filtration assembly, the container configured to contain the water solution being tested by the adjustable filtration assembly;

maintaining, using a pressure gauge, a specific pressure of the water solution in the adjustable filtration assembly during the water filtration test while the water solution passes through the adjustable filtration assembly;

outputting, using an outlet valve of the adjustable filtration assembly when the outlet valve is opened by an end user, a flow meter and totalizer to measure a volume of the water solution from the adjustable filtration assembly during a given time period; and filtering, during the outputting and using a filter membrane mounted in the outlet valve, solids from a measured volume of the water solution; and determining a relative plugging index (RPI) value for the water solution based on a weight of the solids and a length of the given time period, wherein the weight of the solids is determined using the measured volume and a starting wet weight of the filter membrane.

16. The non-transitory, computer-readable medium of claim 15, the operations further comprising releasing, by a relief valve on the adjustable filtration assembly, a portion of the water solution when a pressure of the water solution in the container exceeds a threshold pressure.

17. The non-transitory, computer-readable medium of claim 15, the operations further comprising displaying a current pressure reading of the water solution in the container.

18. The non-transitory, computer-readable medium of claim 15, the operations further comprising receiving, from the end user, adjustments specifying a specific pressure at which to maintain a pressure of the water solution in the container.

19. The non-transitory, computer-readable medium of claim 15, wherein the adjustable filtration assembly is attached to and supported by a stand.

20. The non-transitory, computer-readable medium of claim 15, wherein the sample point is selected from sample points of supply well flowlines, upstream filters, downstream filters, and upstream injection water wells.

* * * * *